US00PP36065P2

(12) United States Plant Patent
Kordes

(10) Patent No.: US PP36,065 P2
(45) Date of Patent: Aug. 13, 2024

(54) MINIATURE ROSE PLANT NAMED 'KORpot130'

(50) Latin Name: *Rosa hybrida*
Varietal Denomination: KORpot130

(71) Applicant: W. KORDES' SÖHNE Rosenschulen GmbH & Co KG, Klein Offenseth-Sparrieshoop (DE)

(72) Inventor: Wilhelm Alexander Kordes, Klein Offenseth-Sparrieshoop (DE)

(73) Assignee: W. KORDES' SÖHNE ROSENSCHULEN GMBH & CO KG, Klein Offenseth-Sparrieshoop (DE)

( * ) Notice: Subject to any disclaimer, the term of this patent is extended or adjusted under 35 U.S.C. 154(b) by 0 days.

(21) Appl. No.: 18/400,251

(22) Filed: Dec. 29, 2023

(51) Int. Cl.
*A01H 5/02* (2018.01)
*A01H 6/74* (2018.01)

(52) U.S. Cl.
USPC ..... Plt./120

(58) Field of Classification Search
USPC ..... Plt./120, 119, 127, 126, 147, 146
CPC . A01H 5/02; A01H 5/00; A01H 6/749; A01H 6/74
See application file for complete search history.

(56) References Cited

U.S. PATENT DOCUMENTS

PP27,162 P2 9/2016 Kordes
PP29,041 P3 3/2018 Kordes

OTHER PUBLICATIONS

CPVO Version 4.18.7 for Rosa Korpot130, retrieved on May 14, 2024 at https://online.plantvarieties.eu/publicConsultationDetails?registerId=20232106&denomination=korpot130, 2 pp. (Year: 2024).*
HelpMeFind Roses, Clematis and Peonies, retrieved on May 14, 2024 at https://www.helpmefind.com/rose/l.php?l=2.79555.2&tab=1, one page. (Year: 2024).*

* cited by examiner

*Primary Examiner* — June Hwu
(74) *Attorney, Agent, or Firm* — Panitch Schwarze Belisario & Nadel LLP; Stephany G. Small; Travis W. Bliss

(57) ABSTRACT

A new and distinct variety of miniature rose plant, referred to by its cultivar name, 'KORpot130', is described. The new variety forms in abundance on a substantially continuous basis attractive, salmon-colored blossoms. The vegetation is glossy, dark green and vigorous, and the growth habit is compact. Attractive ornamental foliage is formed.

1 Drawing Sheet

Latin name of genus and species of plant claimed: *Rosa hybrida.*

Variety denomination: 'KORpot130'.

STATEMENT REGARDING PRIOR DISCLOSURES BY THE INVENTOR

The first offer for sale of the new variety was February 2023. The first offer for sale of the new variety was by the inventor or another who obtained the new variety directly or indirectly from the inventor. No plants of the new variety have been sold in this country or anywhere in the world, nor has any disclosure of the new plant been made, more than one year prior the effective filing date of this application, and such sale or disclosure within one year was either derived directly or indirectly from the inventor.

BACKGROUND OF THE INVENTION

The new variety of miniature rose plant of the present invention was created by controlled breeding in 2018 in Offenseth-Sparrieshoop, Germany by artificial pollination wherein two parents were crossed which previously had been studied in the hope that they would contribute the desired characteristics. The female parent (i.e., the seed parent) of the new variety was an unnamed seedling, which was the product of the cross between 'KORaroma02' (not patented) and 'KORaroma03' (U.S. Plant Pat. No. 29,041). The male parent (i.e., the pollen parent) of the new variety was the 'KORpot050' variety (U.S. Plant Pat. No. 27,162).

The parentage of the new variety can be summarized as follows:

('KORaroma02' x 'KORaroma03') x 'KORpot050'

The seeds resulting from the above pollination were sown and small plants were obtained which were physically and biologically different from each other. Selective study resulted in the identification of a single plant of the new variety.

The new variety has been found to undergo asexual propagation at Klein Offenseth-Sparrieshoop, Germany by a number of routes such as vegetative cuttings. Asexual propagation techniques in Klein Offenseth-Sparrieshoop, Germany, such as vegetative cuttings, have shown that the characteristics of the new variety are homogeneous, stable, and strictly transmissible by such asexual propagation from one generation to another. Accordingly, the new variety undergoes asexual propagation in a true-to-type manner.

SUMMARY OF THE INVENTION

It was found that the new variety of miniature rose plant of the present invention possesses the following combination of characteristics:

(a) forms attractive salmon-colored blossoms,
(b) exhibits a compact growth habit, and
(c) provides glossy, dark green foliage.

The new variety well meets the needs of the horticultural industry. It can be grown to advantage as attractive ornamentation in parks, gardens, public areas, and residential landscapes. Accordingly, it is particularly well suited for growing in the landscape.

The new variety can be readily distinguished from its ancestors. More specifically, the unnamed female parent variety (i.e., the seed parent) provides a flower fragrance, whereas the flower of the new variety provides no fragrance. Additionally, the new variety provides a taller growth habit and larger sized salmon-colored flowers compared to the growth habit and orange-red flowers of the 'KORpot050' variety (i.e., the pollen parent). Moreover, the new variety can be readily distinguished from non-parental related similar varieties. For example, the 'KORpot029' variety (not patented) displays a smaller flower size compared to the new variety.

The new variety has been named the 'KORpot130' variety.

BRIEF DESCRIPTION OF THE PHOTOGRAPHS

The accompanying photograph shows, as nearly true as it is reasonably possible to make the same in a color illustration of this character, a typical specimen of the new variety and blossoms of the new variety. The illustrated rose plant of the new variety was approximately sixteen weeks of age and was grown indoors on its own roots in a 10.5 cm container in Odense, Denmark.

Drawing—illustrates a specimen of the plant displaying flowers at varying points of opening.

DETAILED BOTANICAL DESCRIPTION

The chart used in the identification of colors is that of The Royal Horticultural Society (The R.H.S. Colour Chart, 2015 edition). The terminology which precedes reference to the chart has been added to indicate the corresponding color in more common terms and The R.H.S. Colour Chart designation used herein represents the closest color observed on the majority of the specified botanical feature. The description is based on a one-year-old specimen of the new variety, observed during September, while growing in a one-gallon container on its own roots in a greenhouse in Cochranville, Pennsylvania.

Botanical classification: *Rosa hybrida* cultivar 'KORpot130'.

Commercial classification: Miniature Rose.

Plant:

*Habit*.—Compact.

*Height*.—Approximately 47.0 cm on average from the top of the soil plane in a 1-gallon container.

*Width*.—Approximately 42.0 cm on average.

Branches:

*Stem color*.—Commonly Green Group 143A.

*Length*.—Main stems: approximately 47.0 cm on average. — secondary stems: approximately 30.0 cm on average.

*Diameter*.—Main stems: approximately 7.0 mm on average. — secondary stems: approximately 3.0 mm on average.

*Texture*.—Glabrous.

*Thorns*.—Young thorns: amount is medium; length is approximately 4.0 mm on average; width is approximately 1.0 mm on average at point of attachment; and color is commonly Greyed-Yellow Group 161 A. — old thorns: amount is abundant; length is approximately 5.0 mm on average; width is approximately 2.0 mm on average at point of attachment; and color is commonly Grey-Brown Group 199A.

Leaflets:

*Number*.—3, 5 and 7.

*Shape*.—Ovate; apex is acute; and base is rounded.

*Arrangement*.—Odd-pinnate.

*Margin*.—Serrate.

*Glossiness of upper side*.—Glossy.

*Texture*.—Upper surface: smooth. — under surface: smooth.

*Venation pattern*.—Reticulate.

*Size*.—Terminal leaflet: length is approximately 6.0 cm on average; width is approximately 3.5 cm on average. — lower leaflets: length is approximately 4.0 cm on average; width is approximately 2.6 cm on average. — 5-Leaflet leaf. length is approximately 11.0 cm on average; width is approximately 8.0 cm on average.

Foliage:

*Young foliage*.—Upper surface color: commonly Greyed-Purple Group 183B with venation of Green Group 143B. — under surface color: commonly Greyed-Purple Group 183A with indistinguishable venation.

*Old foliage*.—Upper surface color: commonly Green Group 139A with indistinguishable venation. — under surface color: commonly Green Group 138A with indistinguishable venation.

*Petiole*.—Texture: upper surface is smooth; under surface is mostly smooth with sparse papilla. — length: approximately 2.0 cm on average. — width: approximately 1.0 mm on average. — upper surface color: commonly Green Group 143A. — under surface color: commonly Green Group 143B.

*Rachis*.—Length: approximately 1.7 cm on average. — width: approximately 1.0 mm on average. — upper surface color: commonly Green Group 143A. — under surface color: commonly Green Group 143B.

*Stipules*.—Length: approximately 1.0 mm on average. — width: approximately 3.0 mm on average. — margin: entire to erose. — upper surface color: commonly Green Group 138A. — lower surface color: commonly Green Group 138B.

Inflorescence:

*Number of flowers*.—About 9 to 10 blooms on average on a plant at once.

*Number of blossoms per stem or in a cluster*.—Typically 1 bloom per stem on average.

*Peduncle*.—Color: commonly Green Group 143A. — diameter: approximately 5.0 mm on average. — length: approximately 4.5 cm on average. — surface texture: hispidulous with sparse thorns. — strength: strong.

*Sepals*.—Number: 5. — upper surface color and texture: commonly Green Group 138B, covered in short pubescence. — under surface color and texture: commonly Green Group 141C, hispid with sparse prickles mixed in. — size: length is approximately 2.5 cm on average; width is approximately 8.0 mm on average. — margin: entire with occasional extensions on two or three sepals measuring approximately 3.0 mm in length and less than 1.0 mm in width on average with no undulation. — shape: lanceolate. — apex: acute to aristate. — base: truncate or flat as it joins the receptacle.

*Buds*.—Shape: ovoid. — size: length is approximately 3.2 cm on average; width is approximately 1.3 cm on average. — color (when opening): commonly Orange-Red Group 35A.

*Flower*.—Form: double, globular and reflexed. — profile: reflexed. — diameter: approximately 7.5 cm on average. — height: approximately 3.5 cm on average. — duration: on the plant approximately 20 days. — petal color when first and fully opened: upper surface is commonly Red Group 38A with a basal spot commonly of Yellow Group 8B; under surface is commonly Red Group 39C with no basal spot. — petal color at end of bloom: upper surface is commonly Red Group 38B; under surface is commonly Red Group 38B. — petals reflex one by one: yes.

*Fragrance*.—Sweet.

*Petal*.—Number: 70 on average. — drop: average for the type. — length: inner petals typically 3.0 cm; outer petals typically 3.7 cm. — width: inner petals typically 2.0 mm; outer petals typically 3.0 cm. — overall shape: broadly obovate. — margin: entire with medium undulation. — apex shape: rounded to cuspidate. — base shape: rounded to cuneate. — texture: upper surface is glabrous; under surface is glabrous.

*Petaloids*.—Number: approximately 8 on average. — length: approximately 2.6 cm on average. — width: approximately 1.7 cm on average. — color: upper and under surfaces are commonly Red Group 38A with a basal spot commonly of Yellow Group 8B. — texture: smooth. — margin: variable, entire to erose. — shape: rounded and mostly curving inward. — apex: rounded. — base: cuneate.

*Stamen*.—Number: approximately 50. — anthers: number is approximately 50; color is commonly Greyed-Orange Group 165C; length is approximately 2.0 mm on average; and shape is oval. — filaments: length is approximately 3.0 mm on average and color is commonly Greyed-Yellow Group 160A.

*Pistils*.—Arrangement: separate and free. — number: approximately 65. — style: length is approximately 6.0 mm on average and color is commonly Yellow-White Group 158A at the base, transitioning to Greyed-Orange Group 166A at the apex. — stigma: diameter is less than 1.0 mm on average; shape is fan shaped; color is commonly Yellow-White Group 158A.

*Receptacle*.—Diameter: approximately 7.0 mm on average. — shape: urn shaped. — color: commonly Green Group 143C. — surface texture: covered in sparse prickles.

*Pollen*.—None observed.

*Hips/seed*.—None observed.

Development:

*Vegetation*.—Dark green, vigorous and strong.

*Blossoming*.—Abundant and continuous; blooms may continue year- round if grown inside a warm greenhouse.

*Resistance to diseases*.—Good resistance for powdery mildew (*Sphaerotheca pannosa*) under normal greenhouse growing conditions in Cochranville, Pennsylvania.

*Hardiness*.—Unknown.

The new 'KORpot130' variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of miniature rose plant named 'KORpot130' characterized by the following combination of characteristics:

(a) forms attractive salmon-colored blossoms, (b) exhibits a compact growth habit, and (c) provides glossy, dark green foliage;

substantially as herein shown and described.

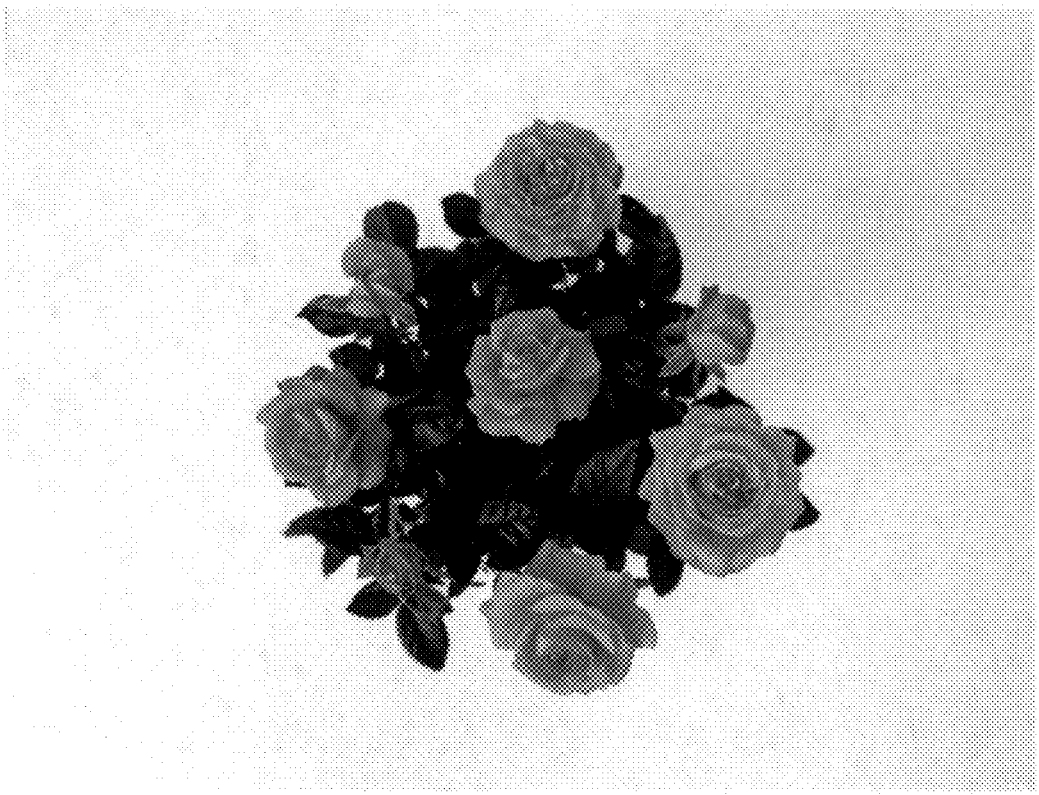

* * * * *